(12) United States Patent
Henderson

(10) Patent No.: US 8,097,467 B2
(45) Date of Patent: Jan. 17, 2012

(54) METHOD FOR THE PRESUMPTIVE DETECTION OF SUBSTANCES

(75) Inventor: Jonathan Paul Henderson, Edinburgh (GB)

(73) Assignee: Heriot-Watt University, Edinburgh (GB)

( * ) Notice: Subject to any disclaimer, the term of this patent is extended or adjusted under 35 U.S.C. 154(b) by 0 days.

(21) Appl. No.: 12/344,094

(22) Filed: Dec. 24, 2008

(65) Prior Publication Data

US 2009/0137049 A1 May 28, 2009

Related U.S. Application Data

(63) Continuation of application No. PCT/GB2007/002448, filed on Jun. 28, 2007.

(30) Foreign Application Priority Data

Jun. 28, 2006 (GB) .................................. 0612793.0

(51) Int. Cl.
*G01N 21/77* (2006.01)
(52) U.S. Cl. .................. 436/169; 436/164; 250/461.1
(58) Field of Classification Search .......................... None
See application file for complete search history.

(56) References Cited

U.S. PATENT DOCUMENTS

| 4,313,736 | A | 2/1982 | Fischer et al. |
| 6,153,147 | A | 11/2000 | Craig |
| 6,242,114 | B1 * | 6/2001 | Yamasaki et al. ............ 428/690 |
| 7,347,972 | B1 * | 3/2008 | Lee ................................. 422/58 |
| 2001/0046710 | A1 | 11/2001 | Cutler |

FOREIGN PATENT DOCUMENTS

| WO | WO00/05579 | 2/2000 |
| WO | WO03/034056 A1 | 4/2003 |
| WO | WO2004/048947 A1 | 6/2004 |

OTHER PUBLICATIONS

Spencer, W.H., et al. The use of salicylic acid, in combination with opium and aconite, for the treatment of acute rheumatism, 1878, British Medical Journal, vol. 2, pp. 163-165.*
Dobson, Kevin D. et al. In situ infrared spectroscopic analysis of the adsrbaption of aromatic carboxylic acid to TiO2, ZrO2, Al2O3, and Ta2O5 from aqueous solution, 2000, Spectrochimica ACTA part A, vol. 56, pp. 557-565.*
PCT Search Report, Serial No. PCT/GB2007/002448, Feb. 6, 2008.
Bradshaw, P. et al. FlexSure Test Device: Qualitative Immunochromatographic Test Format. Clinical Chemistry. 1995. vol. 41, No. 9, pp. 1360-1363.
Wenning, R. et al. Development and Evaluation of Immunochromatographic Rapid Tests for Screening of Cannabinoids, Cocaine and Opiates in Urine. Journal of Analytical Toxicology. Mar. 1998. vol. 22, No. 2, pp. 148-155.

* cited by examiner

*Primary Examiner* — Yelena G Gakh
*Assistant Examiner* — Robert Xu
(74) *Attorney, Agent, or Firm* — Prout International IP, LLC

(57) ABSTRACT

A composition for use in the detection of an intoxicating drug comprising: (i) a first compound that absorbs UV radiation and generates emitted UV radiation at a wavelength absorbable by said intoxicating drug; and (ii) a second compound that absorbs UV radiation emitted by said intoxicating drug upon absorption by said intoxicating drug of said emitted UV radiation and that emits radiation in the visible spectrum is provided. In addition, methods for detecting an intoxicating drug in a sample comprising irradiating with UV radiation a sample contacted with one or two compounds that absorb UV radiation are provided.

19 Claims, 2 Drawing Sheets

METHOD FOR THE PRESUMPTIVE DETECTION OF SUBSTANCES

The present application is continuation under 35 U.S.C. 111 of International Application No. PCT/GB2007/002448 filed on Jun. 28, 2007, which claims priority under 35 U.S.C. §119 to G.B. Application No. 0612793.0 filed on Jun. 28, 2006 the entire disclosures of which are hereby incorporated by reference herein in their entirety.

The present invention relates to a method and device for the presumptive detection of substances, such as narcotics and environmental pollutants within a test sample such as a saliva sample or a drink.

BACKGROUND

Since the introduction of the breathalyser in 1967, much of the uncertainty surrounding the roadside detection of alcohol abuse has been removed.

No such equivalent test, however, exists for intoxicating drugs, including narcotics, in particular for the roadside detection of narcotics in saliva or other bodily fluids. In the United Kingdom, it is a criminal offence to be unfit to drive through drugs when driving or attempting to do so. The drugs in this connection need not be illegal per se to fall within the ambit of this provision. Many prescription and over the counter medications are known to cause intoxication and are provided with instructions warning against driving or operating machinery after consumption.

Police have to depend entirely on subjective behavioural impressions of suspects when deciding whether or not to make an arrest on the basis of intoxication from drugs, including narcotics. The police therefore require a presumptive test for intoxicating drugs, including narcotics, that can be deployed by front-line officers without a requirement for any special training or qualifications.

What the police urgently require is a cheap presumptive indicator of likely intoxication with drugs other than alcohol, which is simple enough for front-line officers to use in the street or at the roadside, allowing full quantitative drug identification to be subsequently carried out in more detail in police laboratories.

Mobile devices for the testing of saliva for drugs do exist but none has yet become widely used, especially by front-line officers. The main reason for this is that all of the current mobile testing methods are based upon monoclonal antibody or immunosensor technology, which is expensive. Within this technology, separate monoclonal antibodies need to be synthesised for each target substance. These cannot be made cheaply. In some cases the immunochromatic signal a generated requires analysis using an expensive electronic device. On a practical level, this technology is currently too expensive to be installed in fleets of patrol cars. Even when electronic reading devices are eliminated and one is simply looking for a colour change on a test stick, there remains an intractably high "cost per test" of around US $20. Using this type of technology on a busy night a single police patrol could spend several hundred pounds on tests.

In addition, electronic monoclonal antibody or immunosensor technologies require the user to handle either sophisticated equipment involving complex keypad input, or a variety of test sticks and strips to cover the range of possible narcotics.

Additionally, these systems can take up to 5 minutes to produce a result.

On a practical level this renders the technology too complicated and time-consuming for use by front-line officers in the street.

The addition of intoxicating drugs, including narcotics, to a person's drink—in order to incapacitate them to facilitate theft or a sexual offense—is of increasing concern. Currently available detection technology is far too expensive and limited in its scope to adequately address this problem.

Similar monoclonal antibody technology to that described above has been applied in the detection of drinks "spiked" with narcotics. However, the roadside monoclonal antibody-based detection apparatus, the costs involved with this technology are high, of the order of £4.99 for 2 testing cards. This high cost is likely to restrict its widespread use.

Furthermore, each card can currently only test for 2 narcotics—gammahydroxybutyrate and ketamine. It cannot detect diphenhydramine.

The present invention addresses one or more of the above-described disadvantages in the art.

SUMMARY OF THE INVENTION

The present invention uses ultraviolet fluorescence rendered visible to the naked eye to indicate the presence of substances in test samples, including the presence of narcotics in saliva or drinks. More broadly, the invention may be used to detect intoxicating drugs (including narcotics and other substances). For example, the present invention is particularly suited to drug testing of athletes and detecting traces of drugs on hands and clothing, and in crime scenes.

The present invention exploits the ultraviolet fluorescence properties of intoxicating drugs to provide a rapid, simple method to test for their presence. The present invention can test for the presence of multiple types of substances in a single test.

Viewed from one aspect therefore the invention provides a composition for use in the detection of an intoxicating drug comprising:
 (i) a first compound that absorbs UV radiation and generates emitted UV radiation at a wavelength absorbable by said intoxicating drug; and
 (ii) a second compound that absorbs UV radiation emitted by said intoxicating drug upon absorption by said intoxicating drug of said emitted UV radiation and that emits radiation in the visible spectrum.

Viewed from a further aspect the invention provides a method for detecting an intoxicating drug in a sample comprising the steps of:
 (i) contacting said sample with a compound that emits visible radiation upon absorption of UV radiation emitted from said intoxicating drug when said intoxicating drug is irradiated with UV radiation; and
 (ii) irradiating said sample and said compound with UV radiation.

Viewed from a further aspect the invention provides a method for detecting an intoxicating drug in a sample comprising the steps of:
 (i) contacting said sample with a compound that absorbs UV radiation and generates emitted UV radiation at a wavelength absorbable by said intoxicating drug, wherein said intoxicating drug emits visible radiation upon absorption of said emitted UV radiation; and
 (ii) irradiating said sample and said compound with UV radiation.

Viewed from a further aspect the invention provides a method for detecting an intoxicating drug in a sample comprising the steps of:

(i) contacting said sample with a first compound that absorbs UV radiation and generates emitted UV radiation at a wavelength absorbable by said intoxicating drug and a second compound that absorbs UV radiation emitted by said intoxicating drug upon absorption by said intoxicating drug of said emitted UV radiation and that emits visible radiation; and (ii) irradiating said sample and said compound with ultraviolet radiation.

Viewed from a further aspect the invention provides a support coated and/or impregnated with a composition comprising a first compound and/or a second compound as defined herein.

Viewed from a further aspect the invention provides the use of UV radiation in the presumptive detection of intoxicating drugs.

BRIEF DESCRIPTION OF THE FIGURES

FIGS. 1 and 2 are representations of the fluorescence exhibited, obtained by converting the actual images to greyscale using a photographic filter and converting the greyscale images to the black and white images shown in the figures by using a Halftone Screen i.e. white dots of varying sizes on a black background.

DETAILED DESCRIPTION OF INVENTION

Figure 1:
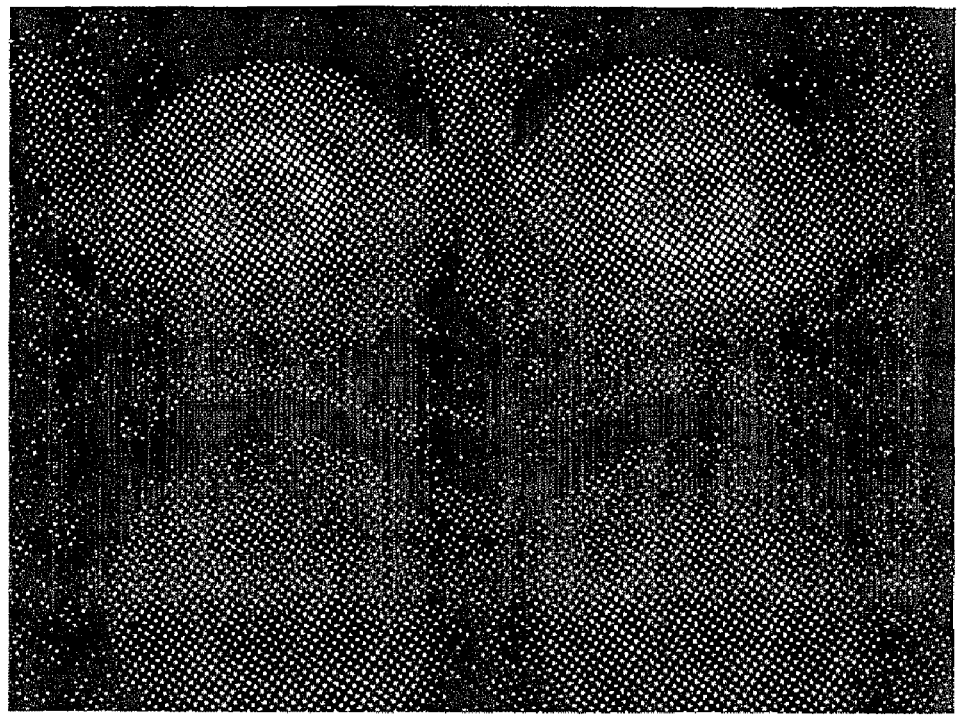
FIG. 1 shows the fluorescence exhibited by 100 ppm heroin (top left), 100 ppm benzoyl ecgonine (top right), 100 ppm caffeine (bottom left), and water (bottom right) when contacted with tantalum (V) oxide and quinine.

The present invention in its various aspects relates to the presumptive detection of intoxicating drugs. As mentioned in the foregoing discussion the detection may not be conclusive with quantitative and conclusive identification being typically carried out in police laboratories. Upon observation of visible fluorescence upon UV irradiation of a sample an intoxicating drug may be presumed to be present in the sample tested.

An intoxicating drug is a compound, typically a synthetic compound, which can lead to intoxication when consumed in sufficient quantity. Intoxication may be defined as a condition of stupefaction or disorder suffered when a sufficient amount an intoxicating substance is consumed. As used herein, an intoxicating drug is not alcohol. Whilst intoxication is a subjective concept, intoxication herein as defined as that according to the NHTSA DWI Detection and Standardized Field Sobriety Testing Participant Manual (2002) which provides three standard tests for determining intoxication (horizontal gaze nystagmus, walk and turn and one leg stand). An intoxicating drug is a drug which can lead to intoxication according to one or more of these tests. Generally although not exclusively, the intoxicating drug will be a narcotic, as defined in the Controlled Substances Act (CSA) in the United States of America. As is known, this Act embraces cocaine and cocoa leaves as narcotics, even although cocaine and cocoa leaves neither bind opiate receptors nor produces a morphine-like effect, which effects are often used as a definition of narcotics.

Examples of classes of intoxicating drugs detectable according to this invention include cannabinoids (e.g. delta-9-tetrahydrocannabinol), benzodiazepines (e.g. nordiazepan and oxazepam), cocaine and cocaine derivatives or metabolites (e.g. cocaine and benzoyl ecognine), amphetamines (e.g. D-amphetamine and equivalents), methyl amphetamine (e.g. MDA and MDMA (ecstasy)), methadone and opiates (e.g. morphine). Another example of a group of classes include opiates, cannabinols, tropane alkaloids, amphetamines, benzodiazepines ergoline derivatives and ethanolamines. Specific examples of intoxicating drugs detectable according to this invention include MDMA (Ecstasy), gammahydroxy butyrate, morphine, 6-monoacetyl morphine, cocaine, cannabinol, codeine, LSD, ketamine and heroin.

In certain aspects, the present invention uses a "converter substance" along with semiconducting materials to render UV fluorescence of an intoxicating drug within a test sample visible to the naked eye.

The method of the present invention typically involves contacting, e.g. by mixing, a test sample with two compounds. The first absorbs UV radiation and generates emitted UV radiation or a wavelength absorbable by the intoxicating drug, if present in the test sample. After absorption of the emitted UV radiation the intoxicating drug emits UV radiation which is absorbed by the second compound which emits visible radiation. Alternatively, only one of the first compounds may be present. The compound omitted in such embodiments may be either the first or second compound as hereinbefore defined. For example, the present invention may operate without the use of the first compound, relying upon the absorption of the UV radiation directly by the intoxicating drug being tested for and its consequent emission of radiation. Alternatively the second compound may be omitted where the intoxicating drug being tested for is known to emit light visible wavelengths when irradiated with UV radiation (LSD is an example of such a substance).

The subsequent discussion focuses upon those embodiments of the invention in which both first and second compounds are present. However it will be appreciated from the foregoing discussion that the invention is not so limited.

The ultraviolet radiation absorption and emission wavelengths of the intoxicating drug being tested for within the test sample is generally known.

The first compound (where present) is a substance with the ability to absorb ultraviolet radiation at one wavelength and emit it at a wavelength around the absorption wavelength of the intoxicating drugs being tested for.

The second compound (where present) is a substance with the ability to absorb ultraviolet radiation around the wavelength at which the intoxicating drug(s) being tested for emits radiation, and emit it at a wavelength within the visible spectrum.

Figure 3:
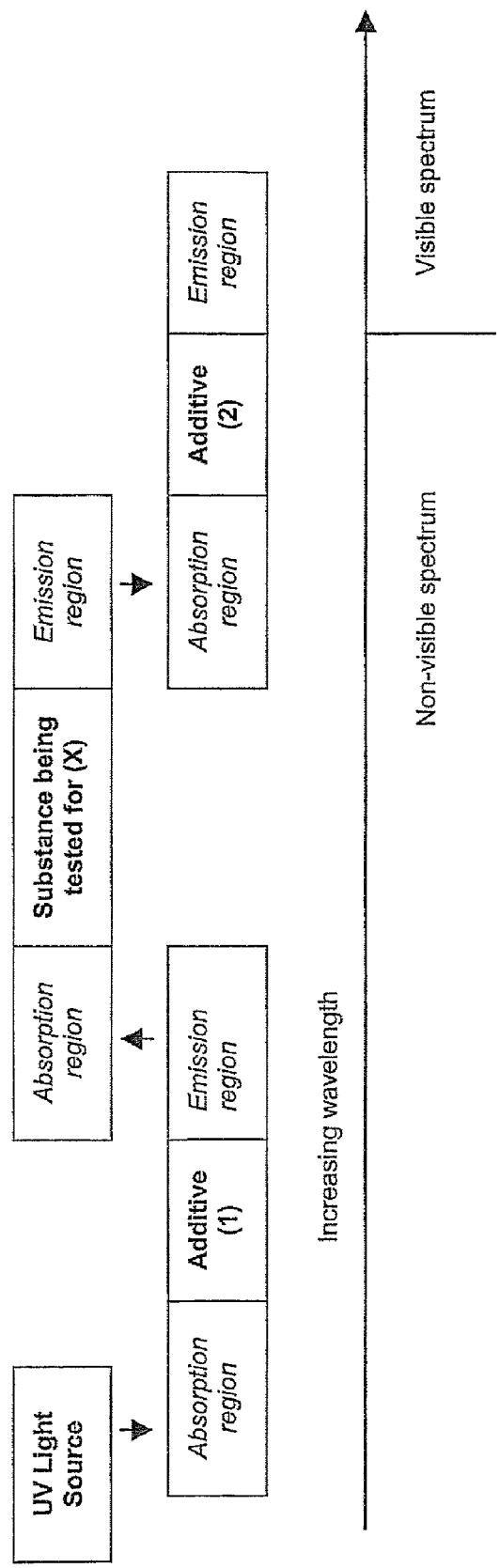
FIG. 3 shows the schematic arrangement of a first compound and a second compound according to certain aspects of this invention (additives (1) and (2)), and light source, for a particular substance being tested for (X) according to one embodiment of the invention.

Preferably the wavelengths at which the first compound emits radiation should not overlap, with the wavelengths at which the second compound absorbs radiation. Preferably the first and second compounds should be chosen according to the absorption and emission wavelengths of the intoxicating drug being tested for, as indicated in FIG. 3.

Following, contacting, e.g. by mixing, the test sample is exposed to ultraviolet light of a wavelength around the absorption wavelength of the first compound, if present, or, where the first compound is not present, at the absorption wavelength of the intoxicating drug the presence or absence of which it is desired to ascertain. By around herein is meant that the wavelength of UV light to which the test sample is exposed is such that the UV absorption by the intoxicating drug, if present, is within 10% of the $A_{max}$, i.e. the wavelength at which maximum absorption occurs.

The first compound (if present) absorbs such radiation and emits radiation at a wavelength at which the intoxicating drug being tested for absorbs. The intoxicating drug being tested for will absorb such radiation, then emit radiation at a wavelength which the second compound absorbs. The second compound absorbs such radiation and then emits radiation within the visible spectrum. Alternatively the second compound may be absent if the intoxicating drug emits radiation within the visible spectrum.

Without the intoxicating drug being tested for being present, because the emission band of the first compound does not cross over the absorption band of the second compound, little or no visible emission of radiation can take place. Thus when visible radiation is present, the intoxicating drug being tested for is presumed to be present.

Tables 1, 2 and 3 indicate the absorption and emission wavelengths of certain substances suitable for use as the first and second compounds, and the absorption and emission wavelengths of certain intoxicating drugs which could be tested for using the present invention.

TABLES

TABLE 1

Absorption and emission wavelengths of various substances suitable for use as the first compound

| Additive (1) | Band gap wavelength (nm) |
|---|---|
| Tantalum oxide | 269 |
| Zirconium oxide | 248 |

TABLE 2

Absorption and emission wavelengths of various intoxicating drugs often tested for

| Substance being tested for | Absorption wavelength peak (nm) | Emission wavelength peak (nm) |
|---|---|---|
| NARCOTICS | | |
| MDMA (Ecstasy) | 286 | 324 |
| Gammahydroxy butyrate | 215 | 365 |
| Morphine | 285 | 335 |
| 6-monoacetyl morphine | 280 | 355 |
| Cocaine | 254 | 315 |
| Cannabinol | 283/276 | 340 |
| Codeine | 280 | 320 |
| LSD | 323 | 433 |
| Ketamine | 215 | 365 |
| Heroin | 210 | 350 |
| TOXINS | | |
| Dioxins | 200-300 | 300-400 |
| Furans | 200-300 | 300-400 |
| 4-chlorophenol | 222 | 365 |

TABLE 3

Absorption and emission wavelengths of various substances suitable for use as the second compound

| Additive (2) | Absorption wavelength (nm) | Emission wavelength (nm) |
|---|---|---|
| Quinine | 250/350 | 450 |
| Salicylic Acid | 310 | 450 |

Preferably, the test sample is exposed to the ultraviolet light under darkened conditions, in order to ensure fluorescence is clearly visible to the naked eye.

As previously mentioned, it is advantageous if the second compound (if present) exhibits negligible absorption around the emission wavelength of the first compound (if present) in order to avoid the risk of the emission wavelengths from the first compound being absorbed directly by the second compound, and thus causing fluorescence of the second compound. Alternatively, if the amount of fluorescence expected from the intoxicating drug after absorption of fluorescence emitted from the first compound is known, it is preferred that any absorption by the second compound of radiation emitted by the first compound and/or of UV radiation from the UV source is less than this known amount of fluorescence. Alternatively, if the amount of fluorescence expected from the intoxicating drug is unknown (as is typically the case), there may be a presumption of the presence of the intoxicating drug if the fluorescence emitted from compound 2 is greater than the sum of that emitted as a result of direct absorption of UV from the UV source by compound 2 and that emitted as a result of direct absorption of UV from that emitted by compound 2. Preferably the fluorescence from compound 2 resulting from the intoxicating drug being tested for is greater than the sum of (i) direct absorption of UV from the UV source (e.g. a UV lamp); and (ii) absorption of emitted UV from compound 1 by compound 2.

The method of the present invention can be used to provide a rapid and simple test for intoxicating drugs, in particular narcotics, particularly a test which may be employed at the roadside. Conveniently, the test may be conducted with saliva samples. However, it will be appreciated that other samples (e.g. liquids) of bodily origin may also be used, for example mammalian (e.g. human) blood, sweat or urine samples.

It will also be appreciated that the present invention may allow detection of metabolites of the compound of interest, where such metabolites have the UV fluorescence characteristics of the compound whose absence or presence it is desired to ascertain.

The method of the present invention can also be used to detect intoxicating drugs including narcotics that have been added to drinks.

Within the roadside drug detection and other embodiments the present invention may be implemented, for example, through impregnating a support material, or support, with, for example, paper (or other suitable material) with the first and second compounds, also referred to herein as additives (1) and (2), and placing a drop of saliva onto such paper. Alternatively the first and or second compounds may be adsorbed or otherwise fixed onto the support. Preferably the support is permeable by the sample under test. The support may be treated in situ, i.e. contemporaneously with practice of a method of the invention. Alternatively, the paper or other material can be pre-treated with the first and/or second compounds of the invention. Moreover, it will be appreciated that practice of the roadside drug detection embodiment is equally appropriate with other embodiments of the invention, for example in the analysis of liquids or other ingestible (comestible or potable) substances suspected to have been contaminated with an intoxicating drug detectable according to the present invention.

Within the drink-testing embodiment, additives (1) and/or (2) may be affixed to an optionally elongate support, made of any suitable material, e.g. paper, cardboard or plastics (e.g. cotton buds), at one end or both ends (particularly where the support is elongate). Examples of such embodiments are straws or "swizzle sticks", preferably using a translucent, non-fluorescent material such as one permeable by the intoxicating drug of interest. Alternatively, a saliva or other sample may be collected first and then contacted with additives (1) and/or (2). Alternatively, in order to carry out a method of the invention, liquid obtained from, for example, swabbing skin (e.g. hands) and/or clothing with wet or alcohol moist absorbent material (e.g. cotton wool or cotton buds) can be applied to, e.g. by dropping onto, a support treated with a composition of the invention. It will be appreciated that this embodiment in likewise suitable in a roadside detection or other scenario.

Alternatively, any convenient support made of any suitable material, e.g. paper, cardboard or plastics (e.g. cotton buds) comprising additives (1) and/or (2) may be optionally housed within a unit, e.g. a disposable unit, into which the saliva or other sample may be introduced prior to exposure to UV irradiation.

Additive (1) is preferably a substance which absorbs ultraviolet radiation at wavelengths of below 300 nm and which emits it at a wavelength in the range of 250-300 nm. A metal oxide semiconductor would generally be suitable. Tantalum (V) oxide is an example of such a substance.

Tantalum oxide absorbs UV radiation at wavelengths below its band gap wavelength of 269 nm and emits radiation at this band gap wavelength.

Additive (2) is preferably a substance which absorbs ultraviolet radiation at wavelengths between 300 nm and 400 nm, and which emits it in the visible spectrum (wavelengths of over 400 nm). Quinine is an example of such a substance. Quinine absorbs ultraviolet radiation at wavelengths of around 350 nm, in addition to at those of around 250 nm, and emits radiation at wavelengths of around 450 nm. Of note is the fact that the emissions of quinine at wavelengths of around 250 nm have very low fluorescence quantum efficiency, resulting mostly in photodegradation rather than fluorescence, whilst the emissions peaking at around 350 nm have a much higher quantum yield. Also, quinine exhibits negligible absorption at wavelengths of 270-300 nm. Quinine is therefore an ideal substance to use as additive (2) due to its relatively strong capacity for absorption within the region of the emissions made by the substance being tested for, as most narcotics of abuse emit ultraviolet radiation between wavelengths of 300 nm and 400 nm, and because its minimum absorption wavelengths mean that its consequent fluorescence is likely to be unaffected by emissions from additive (1), as it absorbs at wavelengths remote from the band gap wavelength of tantalum oxide.

After contacting with the additives the test sample is placed into a dark or near dark chamber. The purpose of this chamber is to allow fluorescence to be visually identified more easily.

The test sample should then be exposed to ultraviolet light. A low pressure Hg vapour lamp emitting UV radiation predominantly at wavelengths below 270 nm would be suitable for use within this embodiment where tantalum oxide and quinine have been used as additives (1) and (2).

Within this and other embodiments the intoxicating drug being tested for is typically a narcotic of abuse. Most narcotics of abuse and their metabolites absorb ultraviolet radiation strongly at wavelengths in the range of 200-300 nm, generally at 250-300 nm and, as mentioned earlier, emit it at wavelengths between 300 nm and 400 nm.

Where the radiation source is the Hg vapour lamp discussed above, ultraviolet radiation is emitted into the darkened chamber with a peak wavelength of 254 nm. Where additive (1) is tantalum oxide, this ultraviolet radiation is absorbed by the tantalum oxide, since tantalum oxide absorbs ultraviolet radiation at wavelengths of 269 nm or less, and emits at its band gap wavelength of 269 nm. Since narcotics of abuse generally absorb radiation at wavelengths in the range of 250-300 nm, this emitted radiation is absorbed by the narcotic of abuse, if present, and subsequently re-emitted at wavelengths between 300 nm and 400 nm. Where additive (2) is quinine, this emitted radiation is absorbed by the quinine, as the peak level at which quinine absorbs ultraviolet radiation is around 350 nm. As quinine emits ultraviolet radiation at wavelengths of around 450 nm, a visible fluorescence will consequently be present. This indicates the presence of narcotics of abuse within the test sample as, if no narcotics of abuse were present, no ultraviolet radiation would be emitted by either the tantalum oxide or test sample within the chamber at a wavelength suitable for absorption, and consequent emission, by the quinine.

The present invention can therefore, by either exhibiting a fluorescence or not, conclusively indicate the presence of narcotics of abuse and other intoxicating drugs, or lack of such presence, in a test sample. With regard to sensitivity, intoxicating drugs can be detected at concentrations as low as 0.5 ppm, for example in the range 0.5 to 1000 ppm, e.g. 0.5 or 1 ppm to 100 ppm.

FIG. 1 indicates the fluorescence exhibited by test samples containing heroin and benzoyl ecgonine (a metabolite of cocaine) placed upon a paper impregnated with tantalum oxide and quinine and exposed to ultraviolet radiation from an Hg vapour lamp similar to that described in the foregoing embodiments. The lower two samples are controls of caffeine and deionised water, showing minimal fluorescence.

The present invention may also be implemented in the form of a straw or a "swizzle stick".

Within this embodiment the straw or "swizzle stick" may be impregnated with a mixture of additives (1) and (2), or adsorbed or otherwise fixed onto the support, such additives chosen according to the properties of the intoxicating drug being tested for, as described in the description of the present invention given above. Within this embodiment, the straw or "swizzle stick" would fluoresce if the liquid being transferred through it were tainted by the intoxicating drug being tested for.

Figure 2:
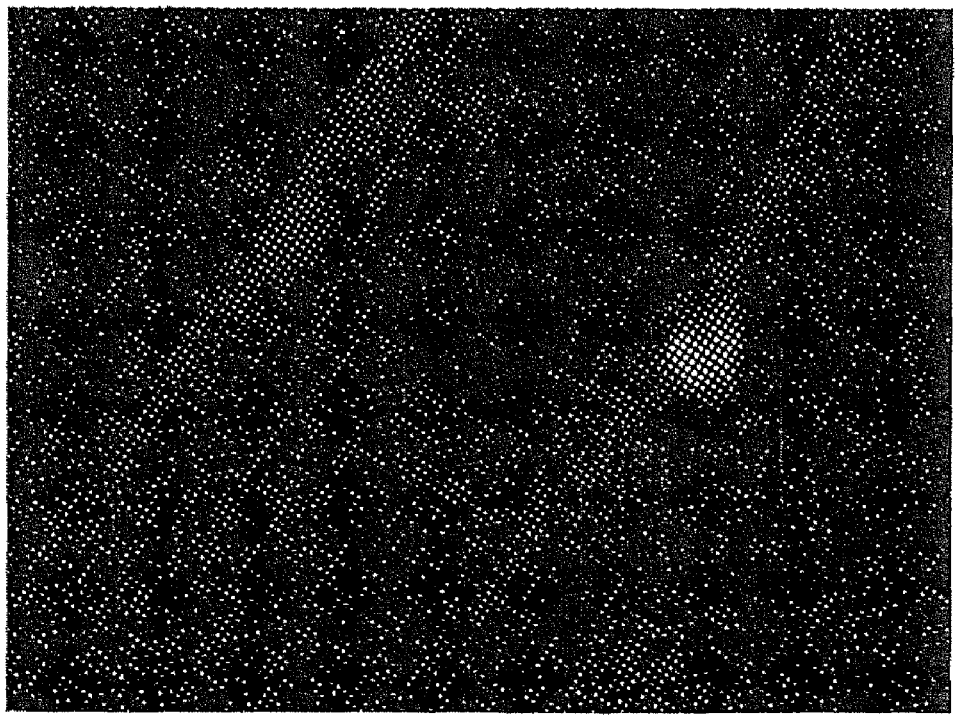
FIG. 2 shows the fluorescence exhibited by modified drinking straws contacted with deionised water (left), and 1000 ppm diphenhydramine (right).

If the same additives as discussed with regard to the previous embodiment were utilized, then fluorescence of the straw or "swizzle stick" would indicate that the liquid in contact with it contained narcotics of abuse or other intoxicating drug. Therefore, this embodiment is be of particular use for identifying drinks which had been spiked with narcotic substances without the knowledge of the drinker. FIG. 2 shows two such modified straws in which tantalum oxide and quinine are fixed to a straw with the inert, non-fluorescent wax methyl stearate (other inert, non-fluorescent waxes may be used), one of which has been in contact with 1000 ppm diphenhydramine, the other a deionised water control.

The present invention may be implemented in a manner consisting of little more than a small UV source in a darkened box. Its implementation therefore has a very low capital cost.

The present invention has a very low operating cost per test. It can be implemented using ordinary small filter papers, straws (e.g. paper straws) or sticks impregnated/coated with a combination of cheap standard laboratory chemicals.

The present invention allows a single test to be performed for multiple substances. It is therefore more cost-effective than separately testing for individual intoxicating drugs. The present invention is also easy to use and provides instant results.

The invention is illustrated by the following non-limiting example:

EXAMPLE

Solutions of 1 ppm in deionised water were prepared for following reagents:
heroin (McFarlan-Smith, Edinburgh, UK)
morphine (McFarlan-Smith, Edinburgh, UK)
benzoyl ecgonine (McFarlan-Smith, Edinburgh, UK)
diphenhydramine (Sigma-Aldrich, Steinheim, Germany)
A 100 ppm solution of salicylic acid (Sigma Aldrich, Steinheim, Germany) and a 1000 ppm solution of diphenhydramine were also prepared.
Detection of a Range of Intoxicants in Water Using Salicylic Acid.

0.5 g of tantalum (V) oxide ($Ta_2O_5$) (Sigma-Aldrich, Steinheim, Germany) was mixed with 10 ml of salicylic acid solution to form a slurry. This was allowed to settle in a cool, dark location for approximately 4 hours. A drop of the thick sediment formed was placed in the centre of 4 1001-030 filter paper discs (Whatman International Ltd, Maidstone, UK). These were then dried in a darkened desiccator overnight. A single drop of the heroin, morphine, benzoyl ecgonine and diphenhydramine solutions were placed on the central spots of 4 of the discs. The $5^{th}$ disc received a drop of deionised water. The discs were then illuminated with a UVGL-58 254 nm Hg-vapour UV source (UVP, Cambridge, UK) in a dark viewing cabinet.
Detection of an Intoxicant Added to a Drink.

0.5 g of tantalum (V) oxide was mixed with 0.5 g of dry quinine with enough of a non-fluorescent wax (methyl stearate, Poole, UK) at 50° C. to form a thick paste. A drop of this paste was then applied near the base of two drinking straws. One was placed in water as a control whilst the other was placed in a 1000 ppm solution of diphenhydramine for 5 minutes. The visible fluorescence is shown in FIG. 2, which shows drinking straws contacted with deionised water (left), and 1000 ppm diphenhydramine (right).

The present invention can also be used to detect other UV fluorescent materials, for example environmental pollutants, food and drinking water contaminants.

Existing technology is only designed to detect particular illegal substances. It is still an offence to drive whilst intoxicated by any substance. Hence, an important area of traffic law is neglected by the prior art, but covered by the present invention.

The invention claimed is:

1. A support impregnated or impregnated and coated, with a composition comprising:
   (i) a first compound that absorbs UV radiation and generates emitted UV radiation at a wavelength absorbable by an intoxicating drug; and
   (ii) a second compound that absorbs UV radiation emitted by said intoxicating drug upon absorption by said intoxicating drug of said emitted UV radiation and that emits radiation in the visible spectrum;
   wherein the first compound is metal oxide semiconductor; and
   the second compound does not absorb said emitted UV radiation.

2. The support of claim 1, which is made of paper, cardboard or plastics material.

3. The support of claim 1, which is elongate and is impregnated, or impregnated and coated only on a portion thereof.

4. The support of claim 1, wherein the intoxicating drug is a narcotic drug.

5. The support of claim 4, wherein the narcotic drug is a cannabinoid, a benzodiazepine, cocaine or a derivative or metabolite thereof, an amphetamine, methyl amphetamine, methadone or an opiate.

6. The support of claim 5, wherein the narcotic drug is MDMA, gammahydroxy butyrate, morphine, 6-monoacetyl morphine, cocaine, cannabinol, codeine, LSD, ketamine or heroin.

7. The support of claim 1, wherein the first compound absorbs radiation at a wavelength of less than 300 nm and generates said emitted UV radiation at a wavelength in the range of 250 to 300 nm.

8. The support of claim 7, wherein the first compound is tantalum oxide or zirconium oxide.

9. The support of claim 1, wherein the second compound absorbs UV radiation at wavelengths between 300 and 400 nm.

10. The support of claim 9, wherein the second compound is quinine or salicylic acid.

11. A support, which is made of paper, cardboard or plastics material, coated, impregnated, or impregnated and coated, with a composition comprising:
   (i) a first compound that absorbs UV radiation and generates emitted UV radiation at a wavelength absorbable by an intoxicating drug; and
   (ii) a second compound that absorbs UV radiation emitted by said intoxicating drug upon absorption by said intoxicating drug of said emitted UV radiation and that emits radiation in the visible spectrum;
   wherein the first compound is metal oxide semiconductor; and
   the second compound does not absorb said emitted UV radiation.

12. The support of claim 11, which is elongate is coated, impregnated, or impregnated and coated only on a portion thereof.

13. The support of claim 11, wherein the intoxicating drug is a narcotic drug.

14. The support of claim 13, wherein the narcotic drug is a cannabinoid, a benzodiazepine, cocaine or a derivative or metabolite thereof, an amphetamine, methyl amphetamine, methadone or an opiate.

15. The support of claim 14, wherein the narcotic drug is MDMA, gammahydroxy butyrate, morphine, 6-monoacetyl morphine, cocaine, cannabinol, codeine, LSD, ketamine or heroin.

16. The support of claim 11, wherein the first compound absorbs radiation at a wavelength of less than 300 nm and generates said emitted UV radiation at a wavelength in the range of 250 to 300 nm.

17. The support of claim 11, wherein the first compound is tantalum oxide or zirconium oxide.

18. The support of claim 11, wherein the second compound absorbs UV radiation at wavelengths between 300 and 400 nm.

19. The support of claim 18, wherein the second compound is quinine or salicylic acid.

* * * * *